US010548622B2

(12) United States Patent
Prestel (10) Patent No.: US 10,548,622 B2
(45) Date of Patent: Feb. 4, 2020

(54) INSTRUMENT, IN PARTICULAR A MEDICAL ENDOSCOPIC INSTRUMENT OR TECHNOSCOPE

(71) Applicant: RICHARD WOLF GMBH, Knittlingen (DE)

(72) Inventor: Stephan Prestel, Rheinstetten (DE)

(73) Assignee: RICHARD WOLF GMBH, Knittlingen (DE)

( * ) Notice: Subject to any disclaimer, the term of this patent is extended or adjusted under 35 U.S.C. 154(b) by 58 days.

(21) Appl. No.: 15/508,687

(22) PCT Filed: Apr. 28, 2015

(86) PCT No.: PCT/DE2015/200284
§ 371 (c)(1),
(2) Date: Mar. 3, 2017

(87) PCT Pub. No.: WO2016/034173
PCT Pub. Date: Mar. 10, 2016

(65) Prior Publication Data
US 2017/0252054 A1 Sep. 7, 2017

(30) Foreign Application Priority Data
Sep. 5, 2014 (DE) .......................... 10 2014 217 796

(51) Int. Cl.
*A61B 17/29* (2006.01)
*A61B 34/00* (2016.01)
(Continued)

(52) U.S. Cl.
CPC ........ *A61B 17/29* (2013.01); *A61B 17/00234* (2013.01); *A61B 34/30* (2016.02);
(Continued)

(58) Field of Classification Search
CPC ...... A61B 2034/305; A61B 2017/2939; A61B 2017/2938; A61B 2017/2927;
(Continued)

(56) References Cited

U.S. PATENT DOCUMENTS

| 5,784,542 A | 7/1998 | Ohm et al. |
| 6,394,998 B1 * | 5/2002 | Wallace ................. A61B 34/71 606/1 |

(Continued)

FOREIGN PATENT DOCUMENTS

| DE | 102012212510 A1 * | 1/2014 | ............. A61B 17/29 |
| DE | 10 2012 219 881 A1 | 4/2014 | |
| WO | 2014/012780 A1 | 1/2014 | |

*Primary Examiner* — Eric J Rosen
*Assistant Examiner* — Andrew P. Restaino
(74) *Attorney, Agent, or Firm* — McGlew and Tuttle, P.C.

(57) ABSTRACT

An instrument, a medical-endoscopic instrument or technoscope, includes a shank (2) and an instrument head (10), which is arranged at a distal shank end of the shank (2) and is bendable relative thereto via a joint. The instrument head (10) includes a tool with two jaw parts (20, 22) which are pivotable relative to one another and are coupled in each case to two pull cables (70, 72, 76), for the control of the jaw parts (20, 22). These pull cables (70, 72, 76), in the region of the joint, are guided around two deflecting rollers (78, 80, 82, 84, 86, 88, 90, 92). Deflecting roller pairs are arranged on both sides of a middle axis (A) of the instrument. Deflecting rollers (82, 84, 90, 92) of a first deflecting roller pair have a smaller diameter than deflecting rollers (78, 80, 86, 88) of a second deflecting roller pair.

13 Claims, 12 Drawing Sheets

(51) Int. Cl.
    *A61B 34/30*     (2016.01)
    *A61B 17/00*     (2006.01)

(52) U.S. Cl.
    CPC ...... *A61B 34/71* (2016.02); *A61B 2017/2927* (2013.01); *A61B 2017/2938* (2013.01); *A61B 2017/2939* (2013.01); *A61B 2034/305* (2016.02)

(58) Field of Classification Search
    CPC ... A61B 17/29; A61B 17/00234; A61B 34/71; A61B 34/30; A61B 2017/00323
    USPC .......................................................... 606/207
    See application file for complete search history.

(56) References Cited

U.S. PATENT DOCUMENTS

| | | | |
|---|---|---|---|
| 2003/0100892 A1 | 5/2003 | Morley et al. | |
| 2007/0208375 A1* | 9/2007 | Nishizawa | A61B 17/29 606/205 |
| 2008/0039255 A1* | 2/2008 | Jinno | A61B 17/062 474/148 |
| 2011/0106145 A1* | 5/2011 | Jeong | A61B 17/29 606/205 |
| 2012/0330287 A1* | 12/2012 | Yim | A61B 34/70 606/1 |

\* cited by examiner

INSTRUMENT, IN PARTICULAR A MEDICAL ENDOSCOPIC INSTRUMENT OR TECHNOSCOPE

CROSS REFERENCE TO RELATED APPLICATIONS

This application is a United States National Phase Application of International Application PCT/DE2015/200284, filed Apr. 28, 2015, and claims the benefit of priority under 35 U.S.C. § 119 of German Application 10 2014 217 796.0, filed Sep. 5, 2014, the entire contents of which are incorporated herein by reference.

FIELD OF THE INVENTION

The invention relates to an instrument and in particular to a medical-endoscopic instrument or technoscope with a shank and with an instrument head which is arranged at a distal shank end, which is bendable relative to the shank via a joint arranged between the shank and the instrument head, wherein the instrument head comprises a tool with two jaw parts, the jaw parts being pivotable relative to one another and coupled in movement in each case to two pull cables for control thereof.

BACKGROUND OF THE INVENTION

The starting point of the invention is formed by shank instruments with an instrument head which is arranged at the distal end of the shank and which can be bent relative to the shank via a joint having one or more joint axes, wherein a jaw tool with two jaw parts which are pivotable relative to one another is provided on the instrument head at the distal side. Instruments of this type, amongst other things are applied in the field of minimal-invasive surgery as forceps, scissors or the like.

It is particularly with the instruments which are applied in the field of minimal-invasive surgery that the cross-sectional dimensions of these are of particular significance. Thus, as a rule, there exists the necessity of keeping the cross section of the shank as small as possible. This is typically the case for all components of the instrument which distally connect onto the shank and which should not project beyond the cross-sectional contour of the shank when the instrument head is aligned in a straight extension with the shank.

SUMMARY OF THE INVENTION

Against this background, it is an object of the invention, to provide an instrument of the previously described type, which meets this requirement concerning as small as possible cross-sectional dimensions, with a simple design construction of the instrument.

The instrument according to the invention is preferably a medical-endoscopic instrument which can be part of a robotic operation system, or an instrument which is to be operated manually. Apart from this, concerning the instrument, it can also be the case of a technoscope which can be applied in difficultly accessible cavities of technical objects. The instrument comprises an elongate, preferably straight and rigidly designed shank. An instrument head which can be bent relative to the shank via a joint arranged between the shank and the instrument head is arranged on the distal end of the shank. The joint can be a joint with one joint axis as well as double joint with two joint axes which are distanced to one another in the longitudinal direction. The instrument head is provided with two jaw parts which are pivotable relative to one another.

The jaw parts are each coupled in movement to two pull cables, for the control of the jaw parts. Each of these pull cables is usefully fastened in each case on an actuation disk which is coupled in movement to the jaw part, wherein the fixation and guidance of the pull cables on the actuation disks is effected in a manner such that the pull cables act antagonistically upon the jaw part. I.e. the connection of the two pull cables to the actuation disk which is assigned to them in each case is effected such that one of the pull cables causes a pivot movement of the jaw part in a first direction when it is loaded in tension, whereby the other pull cable forms a counter player to the first pull cable and causes a counter movement or a pivot movement of the jaw part in the opposite direction when loaded in tension. The pull cables are led through the shaft and are actively connected to a control device at the proximal side of the shank. With regard to the control device, it is the case of a control interface of a robotic system or of a handle which is to be actuated manually, depending on the type of the instrument.

In the region of the joint connecting the instrument head to the shank, the pull cables coupled in movement to the jaw part are each guided around a deflecting roller pair. Each of these deflecting roller pairs comprises two deflecting rollers which rotatably mounted in a manner distanced to one another in the longitudinal direction of the instrument and are aligned to one another in the peripheral direction. One of the pull cables is guided on each of the deflecting roller pairs such that the respective pull cable wraps the two deflecting rollers of a deflecting roller pair in an S-shaped manner, wherein if the instrument head is connected to the shank via a simple joint with one joint axis, the pull cable intersects this joint axis, and if the instrument head is connected to the shaft via a double joint with two joint axes which are distanced to one another, the pull cable is always guided essentially through the instantaneous center of rotation of the bending of the instrument head relative to the shank.

According to the invention, two deflecting roller pairs are arranged in each case on both sides of a middle axis of the instrument, i.e. on outer sides of the middle axis of the instrument which lie opposite one another. Of these two deflecting roller pairs which are arranged in each case at an outer side of the middle axis of the instrument, the deflecting rollers of a first deflecting roller pair have a smaller diameter than the deflecting rollers of a second deflecting roller pair. Hereby, usefully a distal deflecting roller of the first deflecting roller pair and a distal deflecting roller of the second deflecting roller pair have a common rotation axis which is aligned transversely to the longitudinal extension of the instrument, wherein a proximal deflecting roller of the first defection roller pair and a proximal deflecting roller of the second deflecting roller pair have a common rotation axis which is aligned transversely to the longitudinal extension of the instrument. On account of this arrangement of the deflecting rollers of the two deflecting rollers pairs arranged in each case at the outer sides of the middle axis of the instrument which lie opposite one another, and in particular on account of the different diameters of the deflecting rollers of the deflecting roller pairs, one can achieve an arrangement of the deflecting rollers, with which the space within the cross-sectional contour of the instrument and which is only available to a limited extent is able to be utilized in an optimal manner, which in turn permits the cross-sectional dimensions of the instrument to be kept comparatively small.

In this context, it has been found to be particularly advantageous if, as is envisaged according to a first further development of the instrument according to the invention, the first deflecting roller pairs, i.e. the deflecting roller pairs with the deflecting rollers of the smaller diameter, are distanced further to the middle axis of the instrument than the second deflecting roller pairs. On account of this, the deflecting roller pairs can be arranged at a comparatively large distance to the middle axis of the instrument, without the deflecting rollers extending beyond the cross-sectional contour of the shank. Hereby, an adequately large free space for the components of the instrument serving the bending of the instrument head relative to the shank arises in a region around the middle axis of the instrument.

The instrument head is preferably connected to the shank via a double joint, in order to be able to bend the instrument head relative to the shank over an as large as possible angular range. Hereby, a double joint is to be understood as such a joint which comprises at least one joint part pivotable about a pivot axis which is formed at the distal end of the shank and which is hereinafter indicated as the proximal pivot axis, wherein the instrument head at the distal side and on the joint part is pivotable about a second pivot axis which is aligned parallel to the proximal pivot axis and is hereinafter indicated as the distal pivot axis. The instrument head is thus bendable relative to the shank about an angle which is composed of the sum of the pivot angle of the joint part relative to the shank and of the pivot angle of the instrument part relative to the joint part.

In combination with a design, with which the connection of the instrument head to the shank is effected via a double joint, one further advantageously envisages the instrument head being bendable via at least one roller body pairing of a toothed roller body which is arranged at the shank side and a toothed roller body which is arranged on the instrument head side. Accordingly, at least one roller body which is provided with a toothing and which projects on the shank in the direction of the instrument axis head is arranged at the distal end of the shank, whilst at least one further toothed roller body which projects in the direction of the shank and meshes with the roller body arranged on the shank is arranged at the proximal end of the instrument head. The aim of this design lies in ensuring a controlled bending of the instrument head relative to the shank.

According to a further advantageous embodiment of the instrument according to the invention, the joint part which connects the instrument head to the shank is articulated on a joint pin connected to the roller body arranged at the shank side, and on a joint pin connected to the roller body arranged at the instrument head side. Accordingly, the joint pin connected to the shank-side roller body forms the first, proximal pivot axis, about which the joint part is pivotable relative to the shank, and the joint pin which is connected to the instrument-head-side roller body forms the second distal pivot axis, about which the instrument head is pivotable relative to the joint part and relative to the shank.

The first and the second joint pin form the rotation axes for the deflecting rollers of the two deflecting roller pairs which are arranged in each case at the oppositely lying outer sides of the middle axis of the instrument, which is likewise advantageous with regard to the saving of space. I.e. the proximal deflecting rollers of the two deflecting roller pairs are rotatably mounted next to one another at both sides of the middle axis of the instrument, on the first joint pin connected to the roller body arranged at the shank side, whilst the distal deflecting rollers of the two deflecting roller pairs are rotatably arranged next to one another likewise at both sides of the middle axis of the instrument, on the second joint pin connected to the instrument-head-side roller body.

Usefully, in each case a covering part is arranged at the outer side of the deflecting roller pairs which are at the outside with respect to the middle axis of the instrument. This covering part, as with the at least one joint part, is articulated on the two joint pins connected to the roller bodies, and prevents the pull cables which are guided on the first, i.e. radially outer deflecting roller pairs, from coming off in the direction which is away from the middle axis of the instrument.

When using a double joint for the articulation of the instrument head on the shank, an actuation disk which is coupled in movement to a pull cable pair and which is positively connected to the instrument-head-side roller body via a slot nut is preferably provided for bending the instrument head. An elongate hole is provided in each case on the roller body arranged on the instrument head as well as on the actuation disk, for receiving the slot nut. The slot nut preferably forms a receiving space for the joint pin which is connected to the instrument-head-side roller body and which is led through the slot nut. The two pull cables are peripherally guided next to one another in the axial direction of the actuation disk, on this actuation disk, wherein they wrap a distal end of the actuation disk in opposite directions.

The actuation disk is preferably arranged in a common plane with the middle axis of the instrument. This arrangement is advantageous inasmuch as the actuation disk can have a particularly large diameter with this arrangement, without projecting beyond the cross-sectional contour of the shank. Particularly large actuation moments for bending the instrument head can be realized on account of the comparatively large radial dimensions of the actuation disk.

According to a further advantageous embodiment of the instrument according to the invention, two deflecting rollers are arranged successively in the longitudinal direction of the instrument, at the proximal side of the actuation disk, and usefully in a manner aligned to the actuation disk, wherein the pull cables of the pull cable pair, to which pair the actuation disk is coupled in movement, are led through an intermediate space between the deflecting rollers. A particularly effective force transmission for bending the instrument head can be realized by way of this leading of the two pull cables actively connected to the actuation disk. Moreover, the influence of interfering forces acting upon the instrument at the distal side is reduced by way of this.

Two roller bodies which are distanced to one another in the direction transverse to the middle axis of the instrument and which are each engaged with an instrument-head-side roller body are arranged preferably at the shank side, in order to ensure an adequate stability of the roller body connection of the instrument head to the shank. With this design, the actuation disk for bending the instrument head is preferably arranged in the intermediate space between the two roller bodies arranged on the shank side and the two instrument-head-side roller bodies. Hereby, the actuation disk is usefully rotatably mounted on a joint pin passing through the instrument-head-side roller body in a direction transverse to the middle axis of the instrument, which is likewise particularly space-saving.

Further preferably, a joint part is arranged in each case at the outer side of the roller bodies, seen in a direction transverse to the middle axis of the instrument. Hereby, the two joint parts are pivotably movably articulated on the joint pin led through the shank-side roller body in a direction transverse to the middle axis of the instrument, and on the second joint pin led through the instrument-head-side roller body in a direction transverse to the middle axis of the instrument. The two joint pins advantageously radially cover the respective adjacent roller bodies, by which means tissue is prevented from being able to get stuck between roller bodies meshing with one another.

The invention is hereinafter explained in more detail by way of an embodiment example represented in the drawing in a schematically simplified manner and in different scales. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Referring to the drawings, the subsequent embodiments firstly relate only to an instrument which is represented in FIGS. 1-13. With regard to this instrument, it is the case of a medical-endoscopic instrument in the form of a forceps. This instrument which can be an instrument to be actuated manually or one which is used in combination with an operation robot, comprises an elongate, hollow-cylindrically designed shank 2, wherein it is only the distal end of the shank 2 which is represented in the drawing for the purpose of a better overview. The control devices at the proximal end of the shank 2 and which in the case of an instrument to be actuated manually are formed by a handle and in the case of an instrument which is part of a robotic operation system are formed by a control interface of this system, are not shown, since this is counted as belonging to the state of the art and is not the subject matter of the present invention.

An end-piece 4 is arranged at the distal end of the shank 2. As is particularly evident from FIG. 12, in which the end-piece 4 is represented as an individual part, the end-piece 4 has an essentially cylindrical main body 6, onto which a cylindrical section 8 with a smaller diameter connects at the proximal side. The end-piece 4 with the section 8 engages into the distal end of the shank 2, wherein the outer periphery of the section 8 contacts an inner wall of the shank 2. The end-piece 4 is materially connected to the shank 2, in the contact region of the section 8 with the inner wall of the shank 2.

Figure 1:
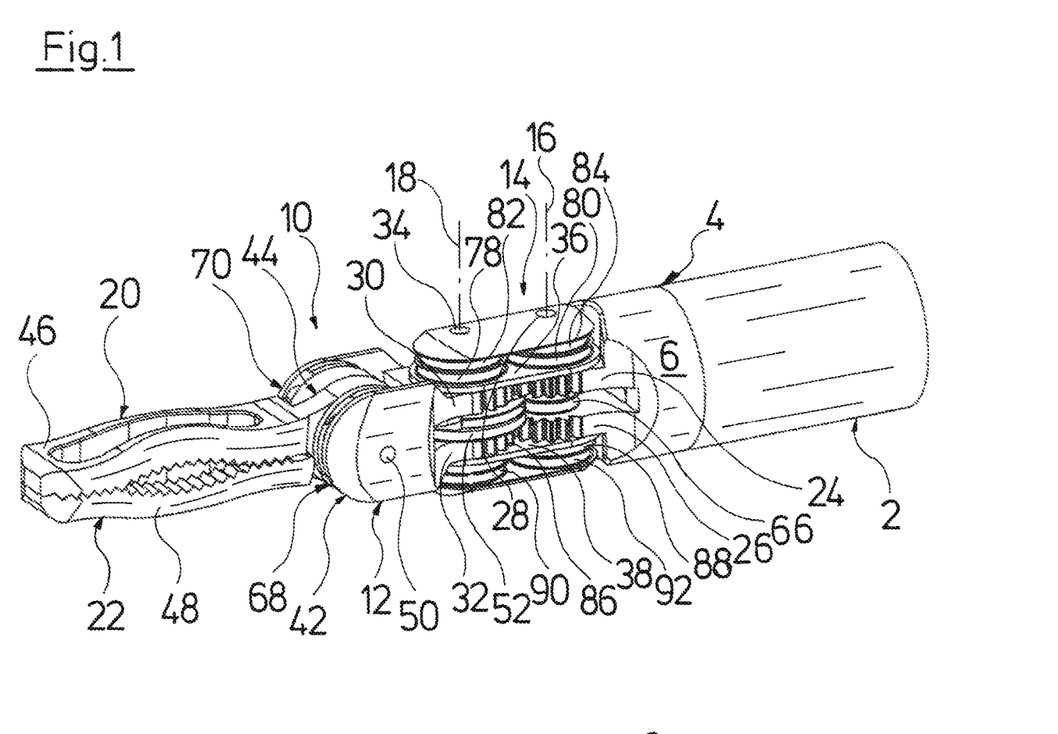
FIG. 1 is a perspective representation of a distal end of an instrument.
Figure 2:
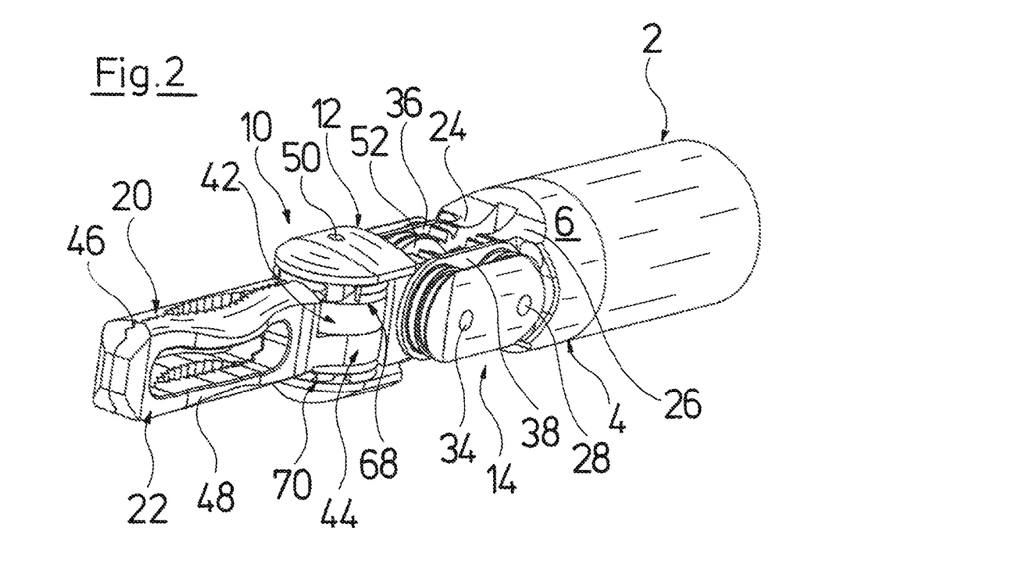
FIG. 2 is a perspective representation of the distal end of the instrument according to FIG. 1, wherein the perspective representation is rotated by 90 with respect to FIG. 1.
Figure 3:
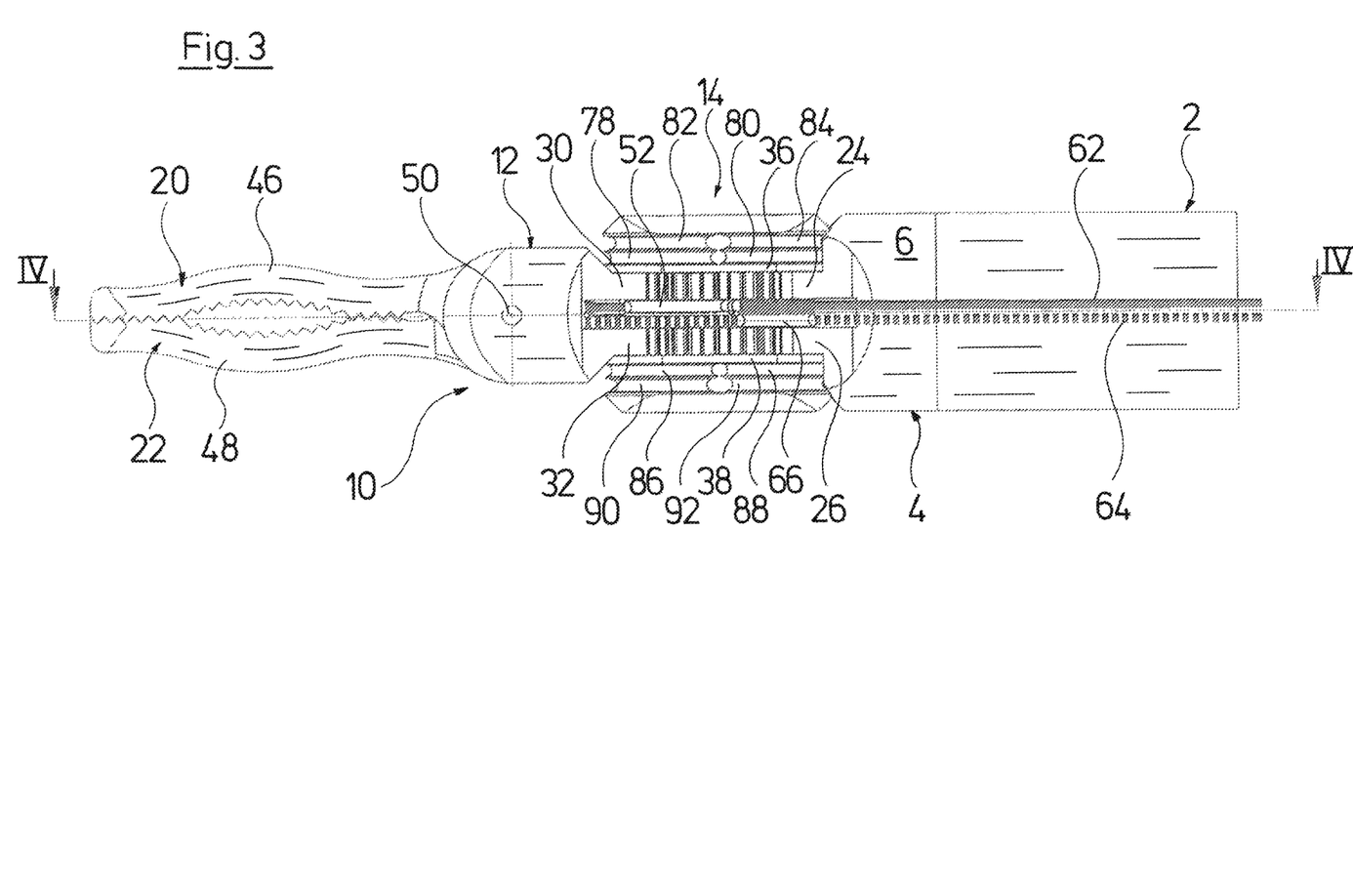
FIG. 3 is a lateral view of the instrument according to FIG. 1.
Figure 4:
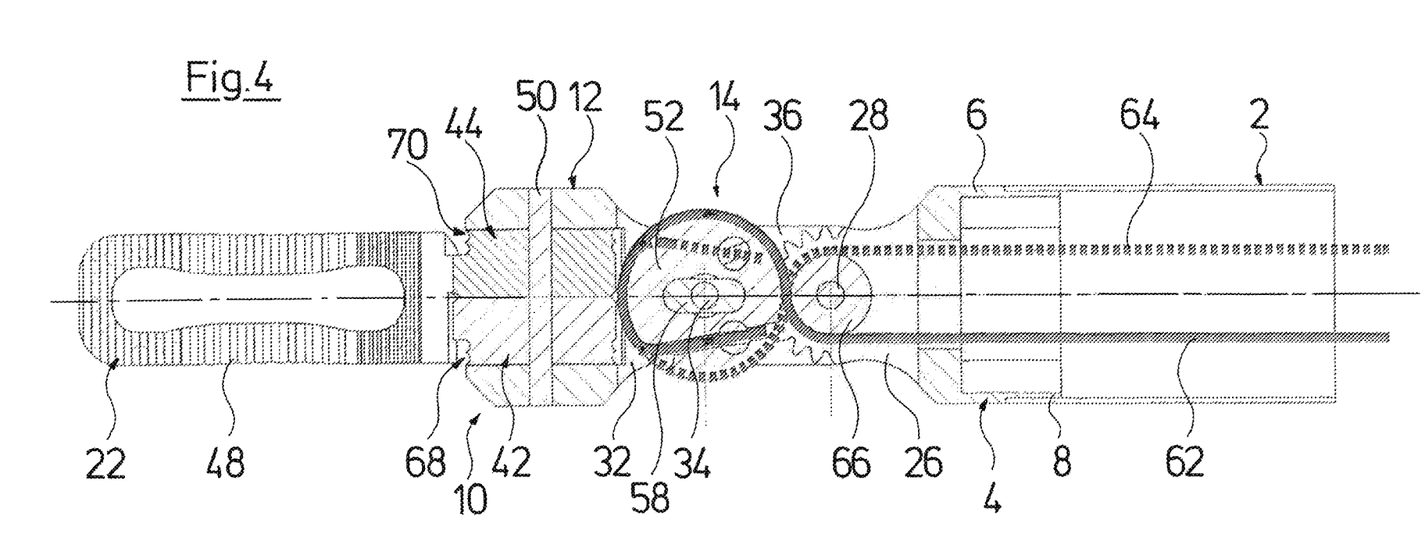
FIG. 4 is a sectioned view along the section line IV-IV in FIG. 3.
Figure 5:
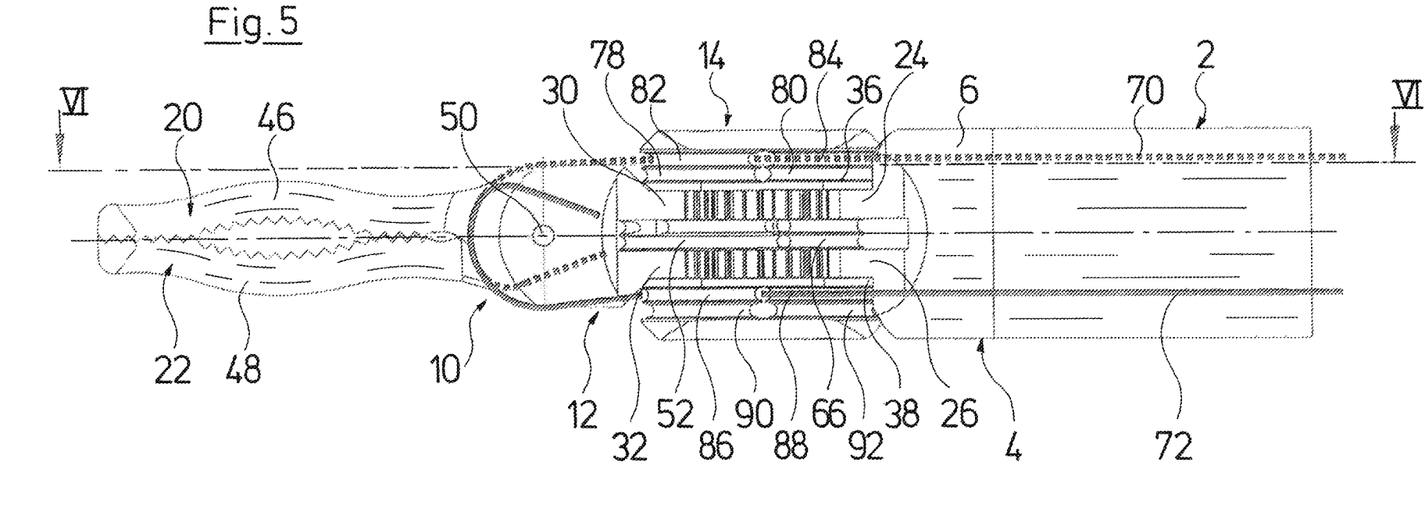
FIG. 5 is a second lateral view of the instrument according to FIG. 1.
Figure 9:
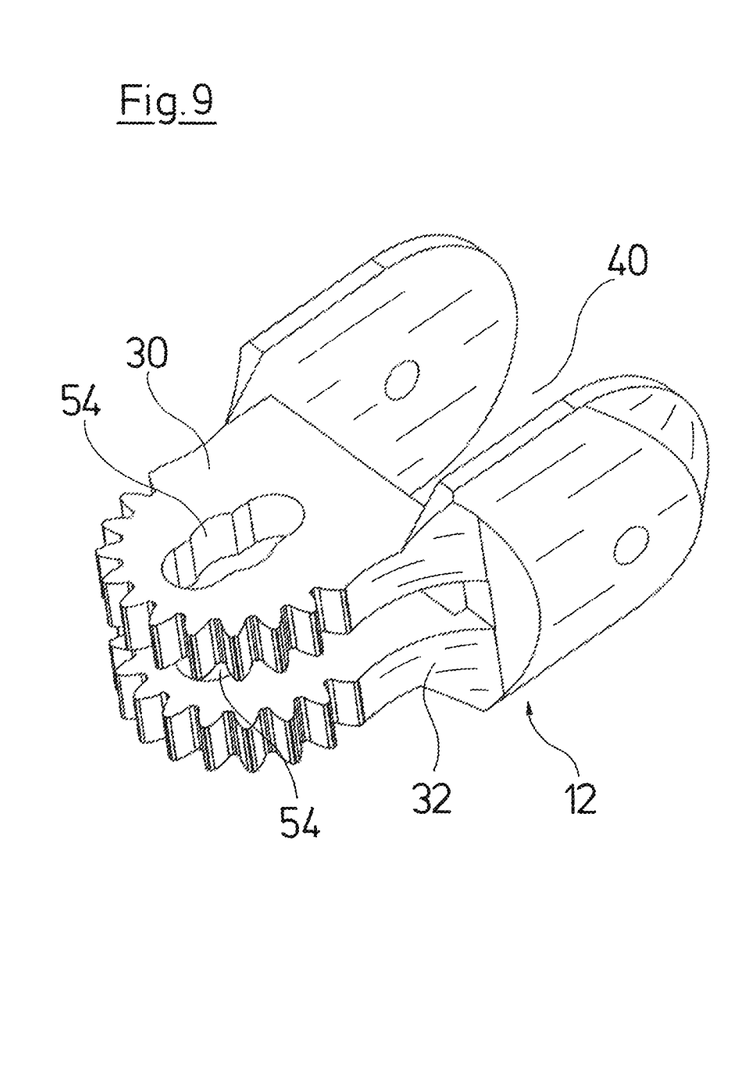
FIG. 9 is a perspective representation of a tool carrier of an instrument head of the instrument according to FIG. 1.
Figure 10:
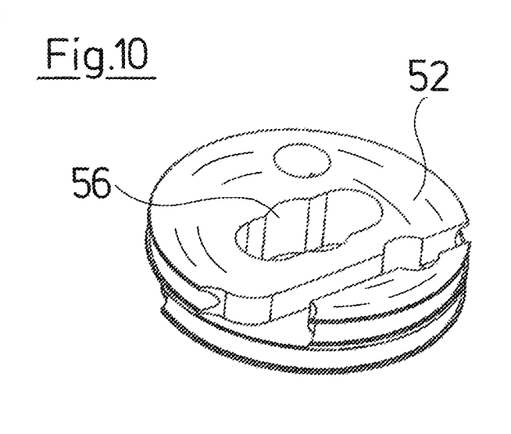
FIG. 10 is a perspective representation of an actuation disk of an instrument head of the instrument according to FIG. 1.
Figure 11:
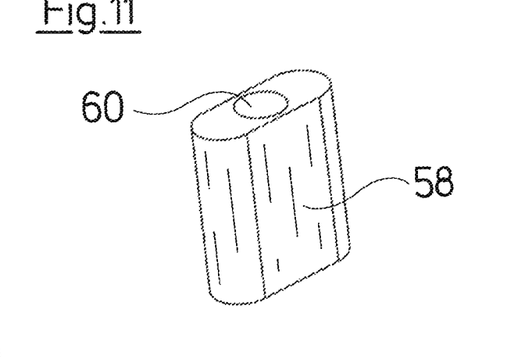
FIG. 11 is a perspective representation of a slot nut for fastening the actuation disk according to FIG. 10, onto the tool carrier according to FIG. 9.
Figure 12:
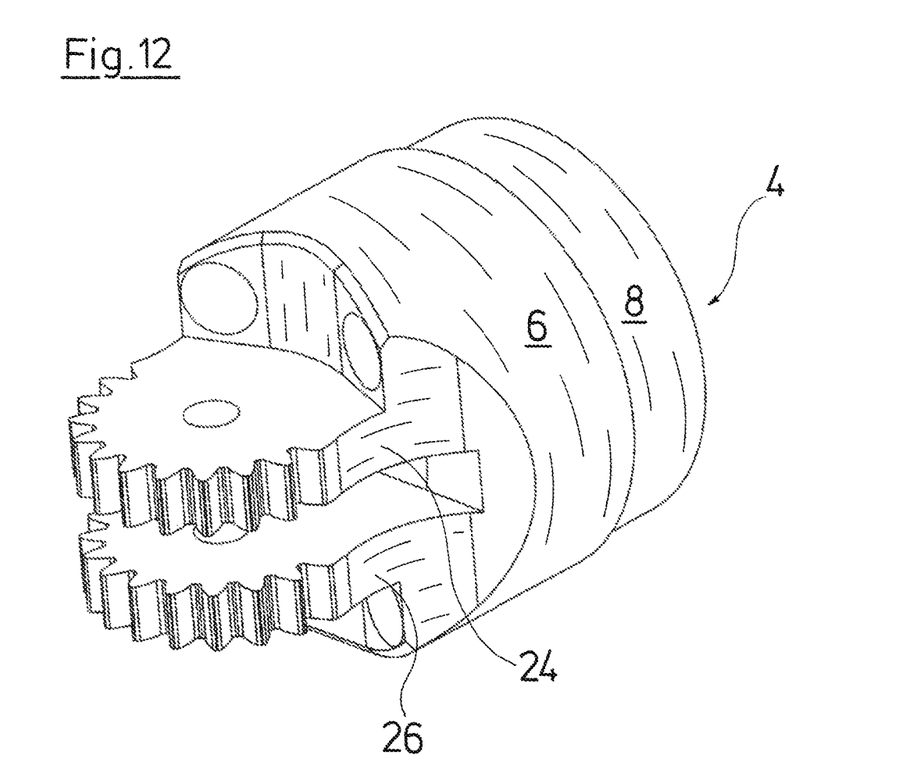
FIG. 12 is a perspective representation of a distal end-piece of a shank of the instrument according to FIG. 1.
Figure 13:
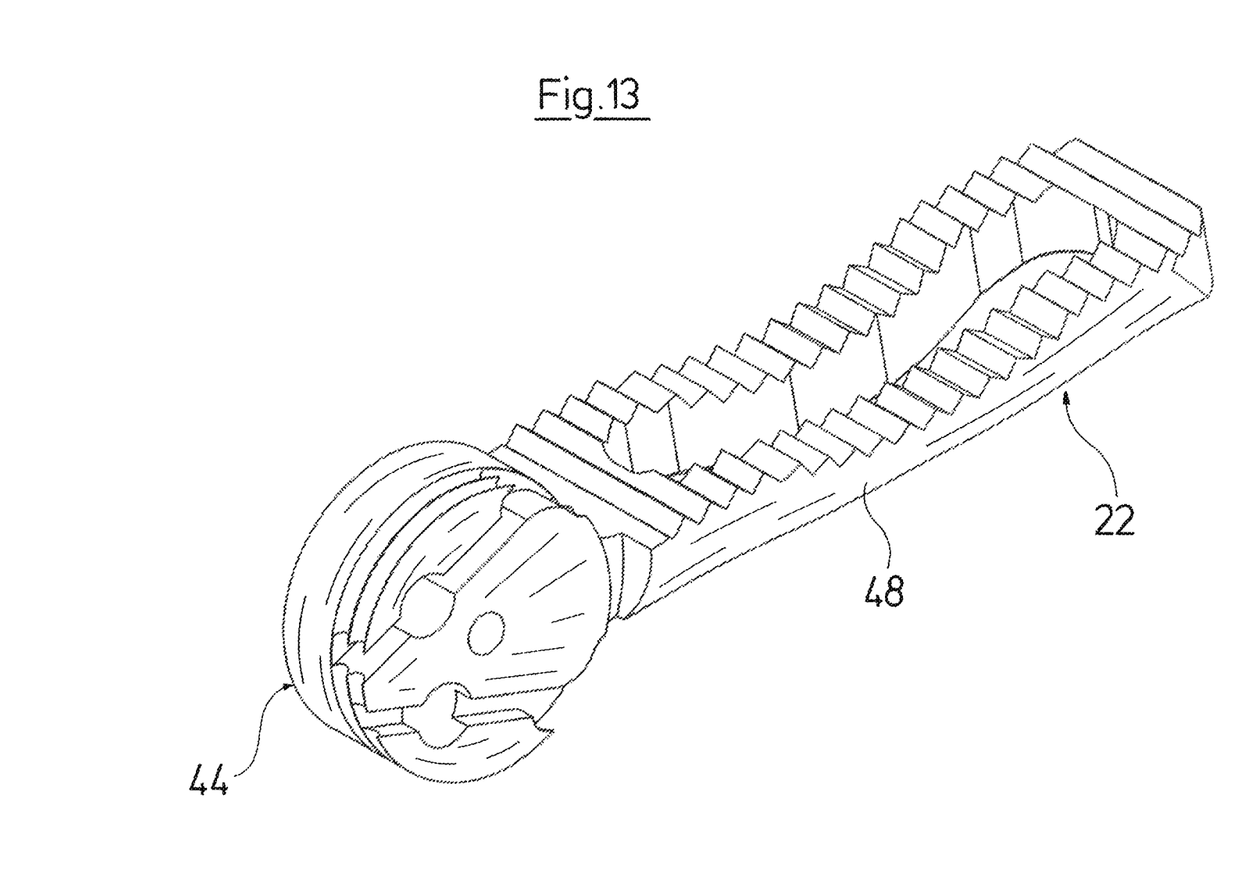
FIG. 13 is a perspective representation of a jaw part of the instrument according to FIG. 1.

An instrument head 10 is arranged at the distal side of the end-piece 4. This instrument head 10 comprises a tool carrier 12 which is represented in FIG. 9 as an individual part and which via a double joint 14 is bendable about a proximal joint axis 16 and about a distal joint axis 18 aligned parallel to the joint axis 16 (FIG. 1). The tool carrier 12 carries a jaw tool with two jaw parts 20 and 22 which are pivotable relative to one another.

The end-piece 4 which is arranged on the distal end of the shank 2, at its distal end comprises two projections 24 and 26 which project in the longitudinal extension of the shank 2 and are distanced to one another in a direction transverse to the longitudinal alignment of the shank 2. A through-hole running transversely to the longitudinal extinction of the shank 2 is formed on the projections 24 and 26 in each case, wherein the through-holes of the two projections 24 and 26 are aligned with one another. The through-holes serve for receiving a joint pin 28 which forms the proximal joint axis 16 of the double joint 14 (FIG. 1).

Two projections 30 and 32 which are distanced to one another and extend in the proximal direction are formed on the proximal end of the tool carrier 12, in a manner corresponding to the two projections 24 and 26 formed on the end-piece 4. A joint pin 34 is also led through the projections 30 and 32 transversely to the longitudinal extension of the tool carrier 12 and forms the distal joint axis 18 of the double joint (FIG. 1).

At the outer side of the projections 24 and 30, a joint part 36 is pivotably movably articulated on the joint pins 28 and 34 which form the joint axes 16 and 18. In a similar manner, a second joint part 38 is pivotably movably articulated on the joint pins 28 and 34, at the outer side of the projections 26 and 32. The joint parts 36 and 38 form a part of the double joint 14 and connect the tool carrier 12 to the shank 2. The tool carrier 12 is therefore bendable relative to the shank 2, in a plane normal to the joint axes 16 and 18, wherein its bending results from the sum of the bending of the joint parts 36 and 38 relative to the shank 2 and of the bending of the tool carrier 12 relative to the joint parts 36 and 38.

The end-piece 4 of the shank 2 and the tool carrier 12 are connected to one another via roller body pairings, in order to permit a defined bending of the tool carrier 12 relative to the shank 2. The distal ends of the projections 24 and 26 formed on the end-piece 4 and the proximal ends of the projections 30 and 32 formed on the tool carrier 12, each comprise a toothed section in the form of a cog segment, for forming these roller body pairings, wherein the toothed sections which are formed on the projections 24 and 26 and the toothed sections which are formed on the projections 30 and 32, which have an identical part-circle diameter, are meshed with one another.

As is particularly evident from FIG. 9, the tool carrier 12 at the distal side comprises an indentation 40 which is open to the distal end of the tool carrier 12. The two jaw parts 20 and 22 of the jaw tool are articulated in this indentation 40. For this, the jaw part 20 comprises a mounting section 42 at the proximal side, and the jaw part 22 comprises a mounting section 44 at the proximal side. A functional section 46 connects distally of the mounting section 42 of the jaw part 20. A functional section 48 likewise connects at the distal side of the mounting section 44 of the jaw part 22, in a manner corresponding to this. The functional sections 46 and 48 of the jaw parts 20 and 22 are formed for gripping bodily tissue or objects. The jaw parts 20 and 22 with their mounting sections 42 and 44, in a manner lying next to one another engage into the indentation 40 formed on the tool carrier 12, where they are pivotably mounted on a pin 50.

An essentially circular actuation disk 52 is arranged on the tool carrier 12, in the intermediate space between the projections 30 and 32. An elongate hole 54 is formed in each case on the projections 30 and 32 of the tool carrier, and an elongate hole 56 is formed on the actuation disk 52, for the positive connection of the actuation disk 52 to the tool carrier 12, wherein the elongate holes 54 and 56 serve received a slot nut 58, via which the actuation disk 52 is fastened on the tool carrier 12. A through-hole 60, through which the joint pin 34 forming the distal longitudinal axis 18 of the double joint 14 is led, is formed on the slot nut 58. As is evident from FIG. 4, two pull cables 62 and 64 are fastened on the actuation disk 52. Two guide grooves which are arranged next to one another in the axial direction of the actuation disk 52 are formed on the outer periphery of the actuation disk 52, for leading or guiding these pull cables 62 and 64. It is also evident from FIG. 4, that the pull cables 62 and 64 at two peripheral sections of the actuation disk 52 which are away from one another are guided to the proximal end of the shank 2 in an antagonistically acting manner, so that a proximally directed tension force upon the pull cable 62 which is exerted there effects a bending of the instrument head 10 in a first direction, and the application of a proximally directed tension force upon the pull cable 64 causes a movement or a bending of the instrument head 10 which is opposite to this bending, in a second direction.

A deflecting roller 66 is rotatably mounted in a manner aligned to the actuation disk 52, at the proximal side of the actuation disk 52, for guiding the pull cables 62 and 64 on the joint pin 28 forming the proximal joint axis 16 of the double joint 14. The pull cables 62 and 64 are led from the actuation disk 52, through an intermediate space between the actuation disk 52 and the deflecting roller 66 in an S-shaped manner, so that the pull cables 62 and 64 come to bear on the deflecting roller 66 at peripheral sections which are away from one another. The actuation disk 52 and the deflecting roller 66 are hereby dimensioned such that the pull cables 62 and 64 are each led through the instantaneous center of rotation of the double joint 14, which has the effect that the bending of the instrument head 10 relative to the shank 2 does not lead to an undesirable length change of the pull cables 62 and 64.

Figure 6:
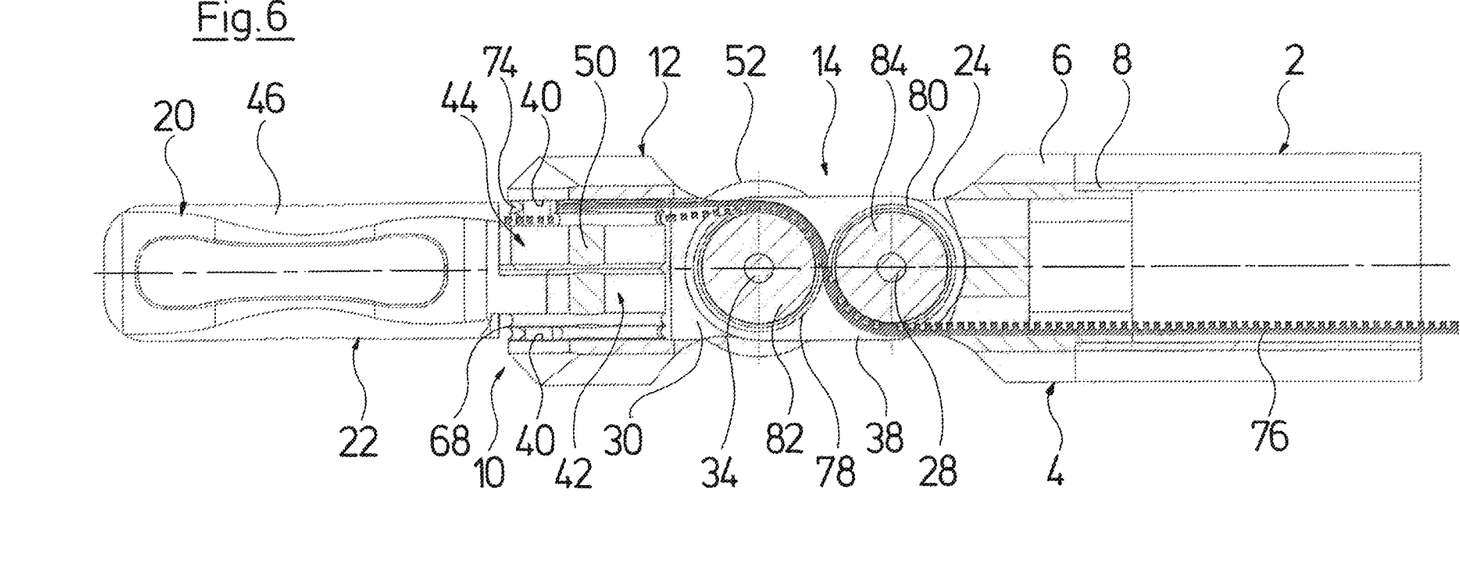
FIG. 6 is a sectioned view along the section line VI-VI in FIG. 5.
Figure 7:
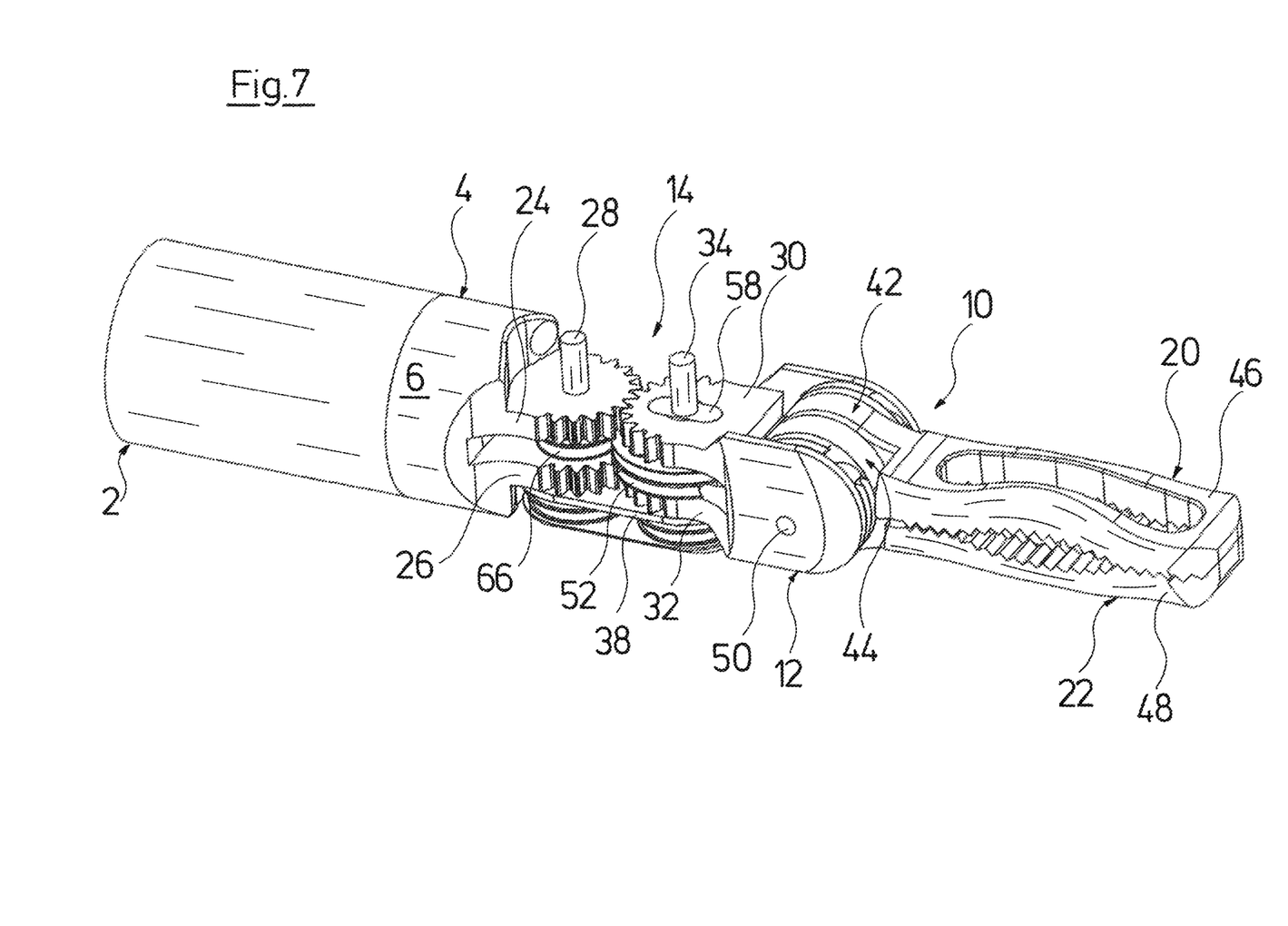
FIG. 7 is a perspective representation according to FIG. 1, omitting certain outer components.
Figure 8:
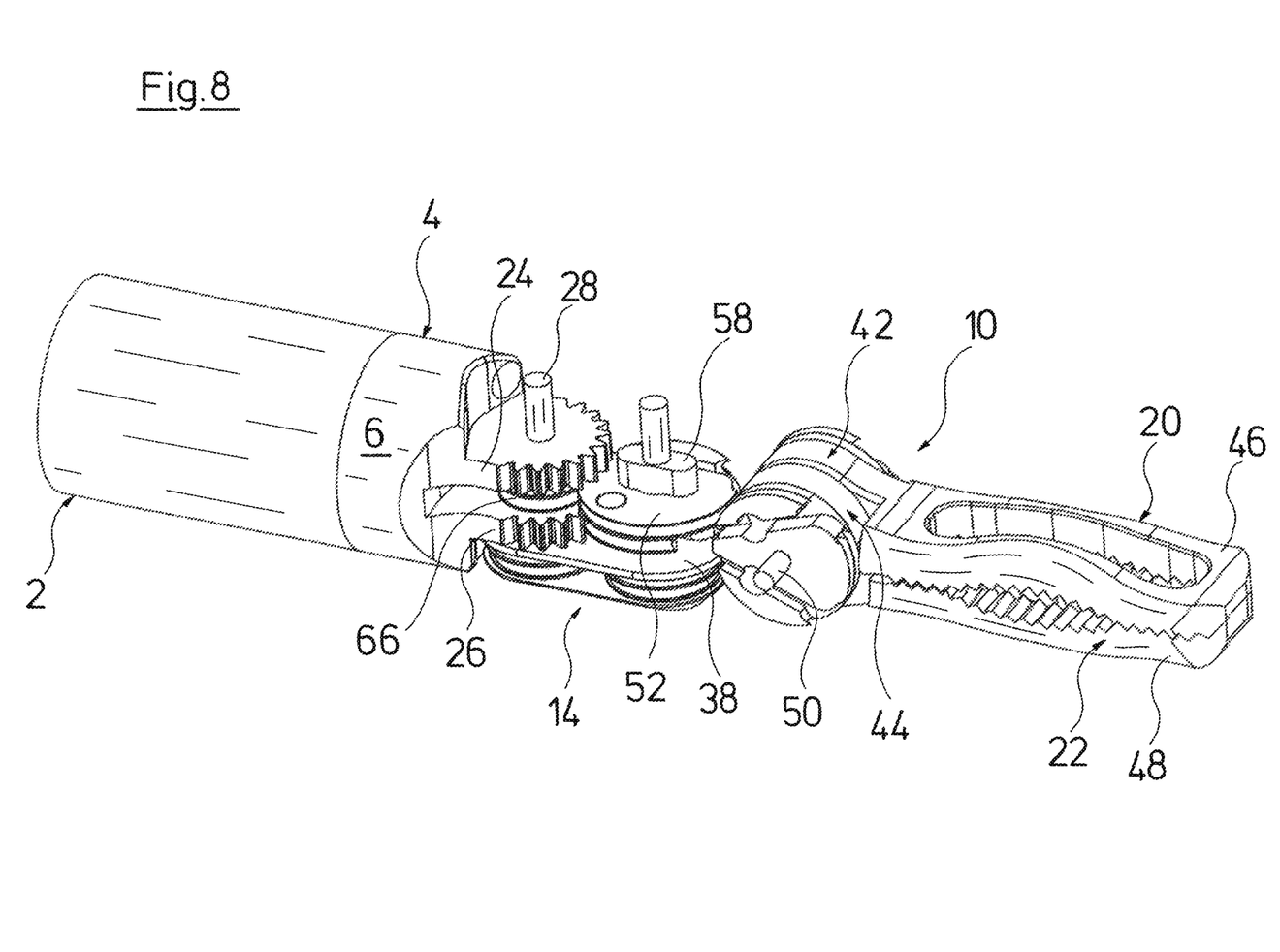
FIG. 8 is a perspective representation according to FIG. 7, omitting further components.

It is to be deduced from FIG. 6 that a region of the mounting section 42 of the jaw part 20 which is directly adjacent the indentation 40 of the tool carrier 12 forms an actuation disk 68 for fastening and guiding two pull cables 70 and 72. The pull cables 70 and 72 represented in FIG. 5 serve for the control of the movement of the jaw part 20. They are guided on the actuation disk 68 in a manner such that they wrap the distal end of the actuation disk 68 in the opposite direction. A region of the mounting section 44 of the jaw part 12 which is adjacent the indentation 40 of the tool carrier 12 also forms an actuation disk 74 for fastening and guiding two pull cables serving for the movement control of the jaw part 22. With regard to these pull cables, only a pull cable 76 is represented in FIG. 6 for the purpose of a better overview in the drawing. This pull cable 76 and the pull cable which is not represented are likewise guided on the actuation disk 74 in a manner such that they wrap the distal end of the actuation disk 74 in the opposite direction.

The pull cables 70 and 72 which are fastened on the actuation disk 68 are led from this actuation disk past the double joint 14, through the shank 2 to the proximal side of the shank 2, where they are coupled in movement to a control device. In a corresponding manner, the pull cable 76 fastened on the actuation disk 74 and the pull cable which is not represented are also led past the double joint 14, through the shank 2 to the proximal side of the shank 2 and there are coupled in movement to a control device.

Each of the four pull cables which serve for the movement control of the jaw parts 20 and 22 is deflected in the region of the double joint, on a deflecting roller pair which is assigned to it, wherein two deflecting roller pairs are provided in each case at both sides of a middle axis A of the instrument. One of these deflecting roller pairs is formed by two deflecting rollers 78 and 80 which have the same outer diameter and which are arranged directly at the outer side of the joint part 36. Hereby, the deflecting roller 78 is rotatably mounted on the joint pin 34, whereas the deflecting roller 80 arranged proximally of the deflecting roller 78 is rotatably mounted on the joint pin 28. The pull cable 76 which is coupled in movement to the jaw part 22 is guided on the deflecting roller pair formed by the deflecting rollers 78 and 80, in a manner such that it wraps the deflecting rollers 78 and 80 in an S-shaped manner and is guided in the intermediate space between the deflecting rollers 78 and 80, through the instantaneous center of rotation of the double joint 14. A deflecting roller 82 is rotatably mounted on the joint pin 34, at the outer side of the deflecting roller 78. This deflecting roller 78 together with a deflecting roller 84 which is rotatably mounted on the joint pin 28, at the outer side of the deflecting roller 80, forms a further deflecting roller pair. The pull cable 70 which is coupled in movement to the jaw part 20 is guided on this deflecting roller pair in a manner such that it wraps the deflecting rollers 82 and 84 in an S-shaped manner and in the intermediate space between the deflecting rollers 82 and 84 is led through the instantaneous center of rotation of the double joint 14. The deflecting rollers 82 and 84 have an identical diameter which however is smaller than the diameter of the deflecting rollers 78 and 80.

Four further deflecting rollers 86, 88, 90 and 92 are arranged at the outer side of the joint part 38, in a manner corresponding to the arrangement of the deflecting rollers 78, 80, 82 and 84 at the outer side of the joint part 36. Hereby, the deflecting roller 86 is rotatably mounted on the joint pin 34 directly at the outer side of the joint part 38 and together with the deflecting roller 88 which is rotatably mounted on the joint pin 28 forms a further deflecting roller pair, on which the pull cable 72 coupled in movement to the jaw part 20 is guided in a manner such that it wraps the deflecting rollers 86 and 88 in an S-shaped manner and in the intermediate space between the deflecting rollers 78 and 80 is led through the instantaneous center of rotation of the double joint 14. Finally, the deflecting rollers 90 which at the outer side of the deflecting roller 86 are rotatably mounted on the joint pin 34 and the deflecting roller 92 which at the outer side of the deflecting roller 88 is rotatably mounted on the joint pin 28 form a deflecting roller pair for the pull cable which is not represented in the drawing and which is coupled in movement to the jaw part 22. The pull cable which is not represented is guided on the deflecting roller pair formed by the deflecting rollers 90 and 92, in the same manner as the pull cable 72 is guided on the deflecting roller pair formed by the deflecting rollers 86 and 88. The deflecting rollers 90 and 92 have a smaller diameter than the deflecting rollers 86 and 88.

Figure 14:
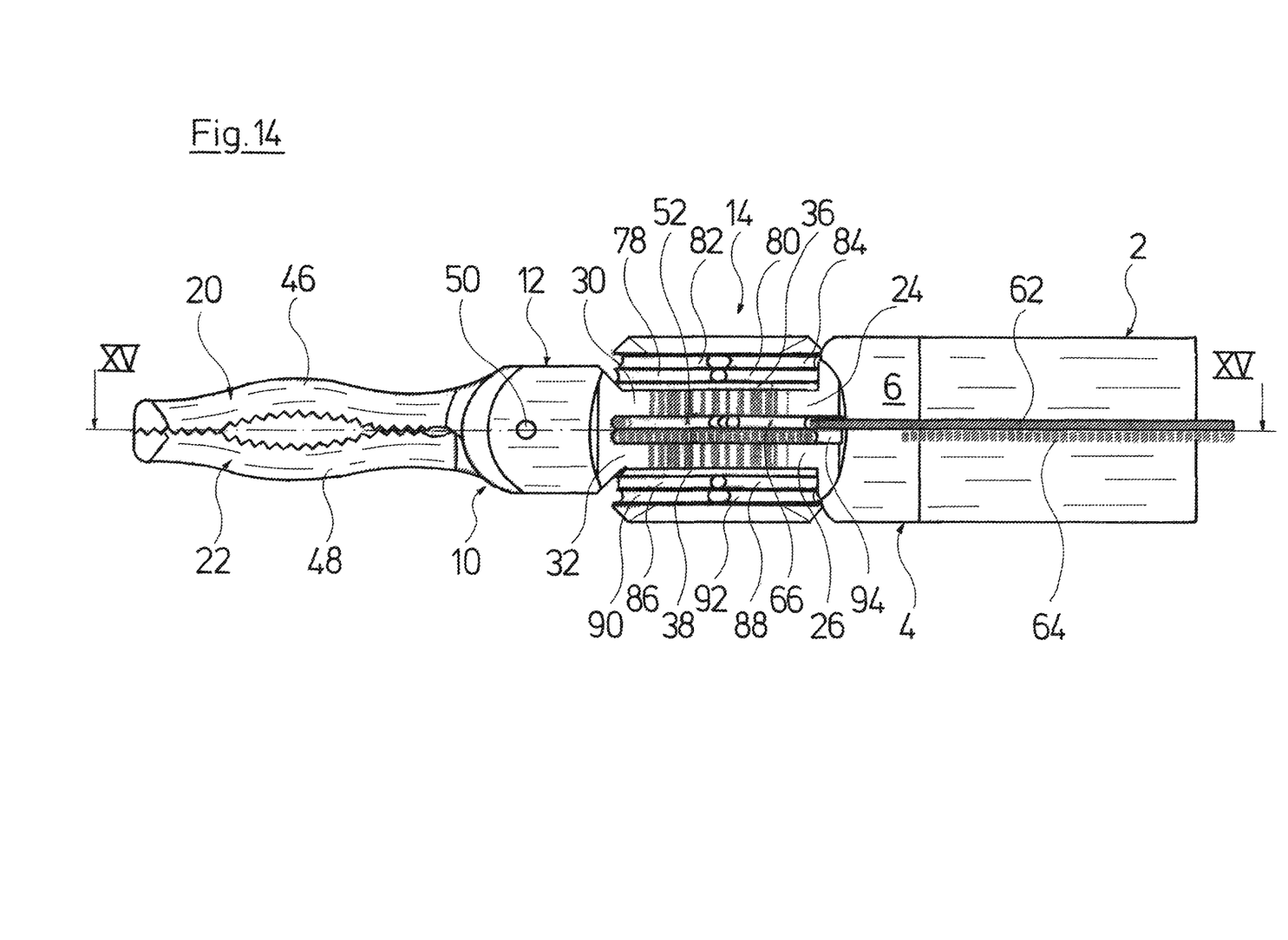
FIG. 14 is a lateral view of the instrument according to FIGS. 1-13, according to a second embodiment example.
Figure 15:
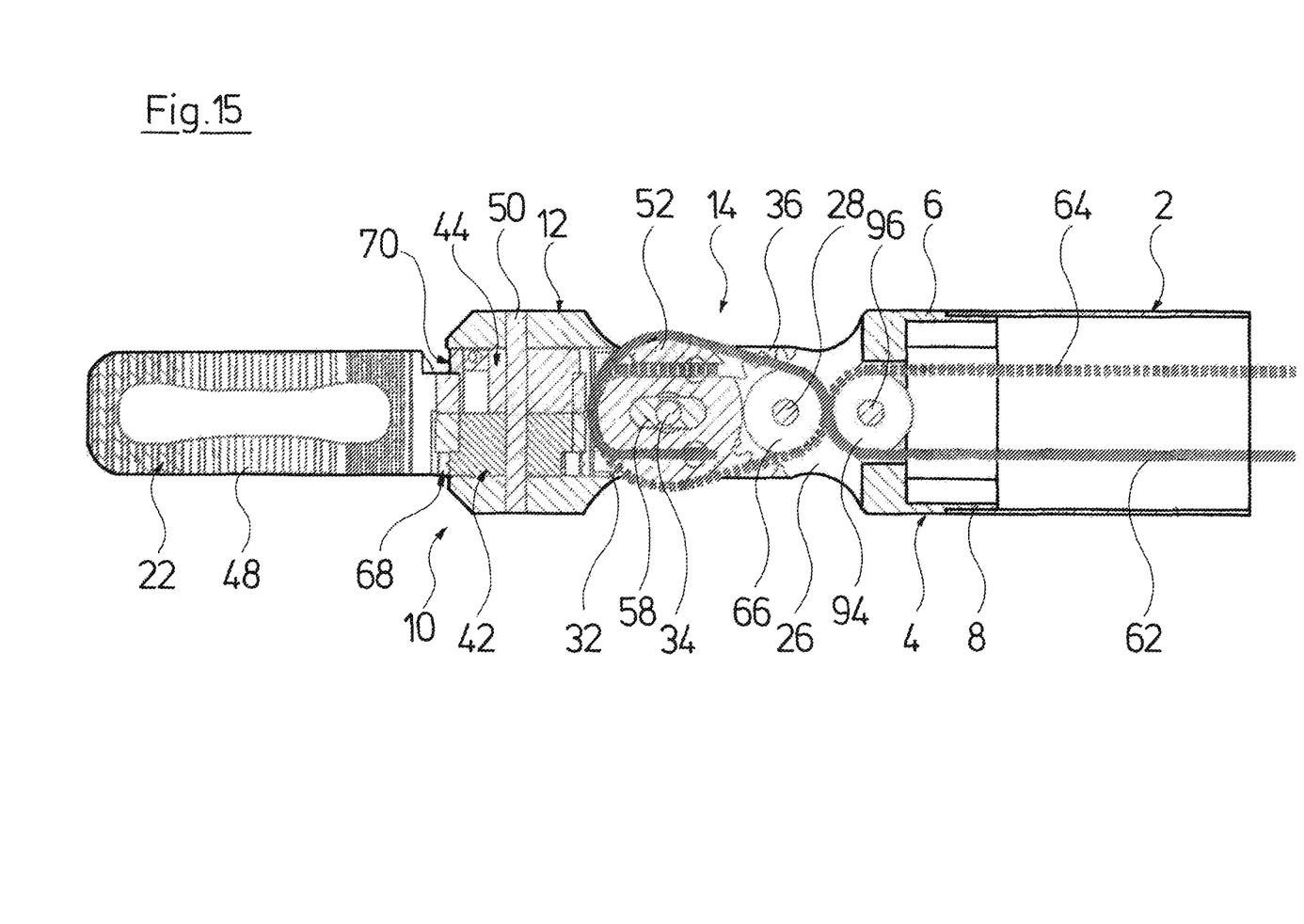
FIG. 15 is a sectional view along the section line XV-XV in FIG. 14.

The instrument which is represented in FIGS. 14 and 15 differs from that instrument represented in FIGS. 1-13 merely with regard to the guiding of the pull cables 62 and 64 which are connected to the actuation disk 52. Here, a further deflecting roller 94 is rotatably mounted on a joint pin 96, at the proximal side of the deflecting roller 66 and on end-piece 4 of the shank 2, in a manner aligned to the actuation disk 52 and the deflecting roller 66. Differently to the instrument represented in FIGS. 1-13, with the instrument represented in FIGS. 14 and 15, the pull cables 62 and 64 which are fastened on the actuation disk 52 are not led through the intermediate space between the actuation disk 52 and the deflecting roller 66, but led in opposite directions through the intermediate space between the deflecting rollers 66 and 94.

While specific embodiments of the invention have been shown and described in detail to illustrate the application of the principles of the invention, it will be understood that the invention may be embodied otherwise without departing from such principles.

The invention claimed is:

1. An instrument comprising:
   a shank;
   an instrument head arranged at a distal end of the shank;
   a joint arranged between the shank and the instrument head, wherein the instrument head is bendable relative to the shank via the joint arranged between the shank and the instrument head and the instrument head comprises a tool with two jaw parts, said jaw parts being pivotable relative to one another;
   a first pair of pull cables, wherein each of the jaw parts is coupled in movement in each case to the first pair of pull cables for control of the jaw parts;
   a second pair of pull cable coupled to a first one of the jaw parts, wherein one pull cable of the second pair of pull cables is guided around a first deflecting roller pair and another pull cable of the second pair of pull cables is guided around a second deflecting roller pair;
   a third pair of pull cables coupled to a second one of the jaw parts, wherein one pull cable of the third pair of pull cables is guided around a third deflecting roller pair and another pull cable of the third pair of pull cables is guided around a fourth deflecting roller pair;
   wherein each of the deflecting roller pairs comprises two deflecting rollers which are arranged next to one another in a longitudinal direction of the instrument, wherein the first and third roller pairs are arranged on a first side of a middle axis of the instrument and the second and fourth roller pairs are arranged on a second side of a middle axis of the instrument deflecting rollers of the first and fourth roller pairs have a smaller diameter than deflecting rollers of the second and third roller pairs, the joint comprising a double joint and the instrument head being connected to the shank via the double joint, the instrument head being bendable via at least one roller body pairing, the at least one roller body pairing comprising a first roller body pairing of a toothed roller body arranged at the shank side and of a toothed roller body arranged at the instrument head side, wherein the joint comprises at least one joint part which connects the instrument head to the shank and is articulated on a first joint pin connected to the toothed roller body arranged at the shank side, and on a second joint pin connected to the toothed roller body arranged at the head side, wherein an actuation disk, which is coupled in movement to the first pair of pull cables, is positively connected to the toothed roller body arranged at the head side via a slot nut.

2. The instrument according to claim 1, wherein the first and fourth deflecting roller pairs are distanced further from the middle axis of the instrument than the second and third roller pairs.

3. The instrument according to claim 1, wherein the first and the second joint pin form rotation axes for the deflecting rollers of the deflecting roller pairs.

4. The instrument according to claim 1, wherein a covering part is arranged at the outer side of the first and fourth deflecting roller pairs which is at the outside with reaped to the middle axis of the instrument.

5. The instrument according to claim 1, wherein die actuation disk is arranged in a common plane with the middle axis of the instrument head.

6. The instrument according to claim 1, wherein the first pair of pull cables coupled in movement to foe actuation disk are led through an intermediate space between the second and third deflecting pairs.

7. The instrument according to claim 1, wherein the at least one roller body pairing further comprises a second roller body pairing of a toothed roller body arranged at the shank side and a toothed roller body arranged at the head side, wherein the first and the second roller body pairings are distanced from one another in the direction transverse to the middle axis, wherein the toothed roller bodies arranged at the shank side engage the toothed roller bodies arranged at the head side.

8. The instrument according to claim 7, wherein the actuation disk is arranged in an intermediate space between the first and the second roller body pairings.

9. The instrument according to claim 7, wherein the joint further comprises a joint part which radially coven the toothed roller bodies and is arranged in each case at the outer side of the toothed roller bodies in the direction transverse to the middle axis of the instrument.

10. The instrument according to claim 1, wherein each of the deflecting roller pairs comprises a first deflecting roller and a second deflecting roller, the first deflecting roller being located adjacent to the second deflecting roller in a direction parallel to the middle axis.

11. The instrument according to claim 10, wherein, for each of the deflecting roller pairs, the first deflecting roller comprises a first deflecting roller longitudinal axis, the second deflecting roller comprising a second deflecting roller longitudinal axis, each of the first deflecting roller longitudinal axis and the second deflecting longitudinal axis being oriented in a direction traversing the middle axis, the first deflecting roller longitudinal axis being located at a spaced location from the second deflecting roller longitudinal axis.

12. An instrument comprising:
   a shank;
   an instrument head arranged at a distal end of the shank;

a joint arranged between the shank and the instrument head, wherein the instrument head is bendable relative to the shank via the joint arranged between the shank and the instrument bead and the instrument head comprises a tool with two jaw parts, said jaw parts being pivotable relative to one another;

a first pair of pull cables, wherein each of the jaw parts is coupled in movement in each case to the first pair of pull cables for control of the jaw parts;

a second pair of pull cables coupled to a first one of the jaw parts, wherein one pull cable of the second pair of pull cables is guided around a first deflecting roller pair and another pull cable of the second pair of pull cables is guided around a second deflecting roller pair;

a third pair of pull cables counted to a second one of the jaw parts, wherein one pull cable of the third pair of pull cables is guided around a third deflecting roller pair and another pull cable of the third pair of pull cables is guided around a fourth deflecting roller pair;

wherein each of the deflecting roller pairs comprises two deflecting rollers which are arranged next to one another in a longitudinal direction of the instrument, wherein the first and third roller pair are arranged on a first side of a middle axis of the instrument and the second and fourth roller pairs are arranged on a second side of a middle axis of the instrument, deflecting rollers of the first and fourth roller pairs have a smaller diameter than deflecting rollers of the second and third roller pairs, the joint comprising a double joint and the instrument head being connected to the shank via the double joint, the instrument head being bendable via at least one roller body pairing, wherein the at least one roller body pairing comprises a first roller pairing of a toothed roller body arranged at the shank side and of a toothed roller body arranged at the instrument head side, wherein the at least one roller body pairing further comprising a second roller body pairing of a toothed roller body arranged at the shank side and a toothed roller body arranged at the head side, wherein the first and the second roller body pairings are distanced from one another in the direction transverse to the middle axis, wherein the toothed roller bodies arranged at the shank side engage the toothed roller bodies arranged at the head side, wherein an actuation disk is arranged in an intermediate space between the two toothed roller bodies arranged at the shank side and the two toothed roller bodies arranged al the instrument head side.

13. An instrument comprising:

a shank;

an instrument head arranged at a distal end of the shank;

a joint arranged between the shank and the instrument head, wherein the instrument head is bendable relative to the shank via the joint arranged between the shank and the instrument head and the instrument head comprises a tool with two jaw parts, said jaw parts being pivotable relative to one another;

a first pair of pull cables, wherein each of the jaw parts is coupled in movement in each case to the first pair of pull cables for control of the jaw parts;

a second pair of pull cables coupled to a first one of the jaw parts, wherein one pull cable of the second pair of pull cables is guided around a first deflecting roller pair and another pull cable of the second pair of pull cables is guided around a second deflecting roller pair;

a third pair of pull cables coupled to a second one of the jaw parts, wherein one pull cable of the third pair of pull cables is guided aramid a third deflecting roller pair and another pull cable of the third pair of pull cables is guided around a fourth deflecting roller pair;

wherein each of the deflecting roller pairs comprises two deflecting rollers which are arranged next to one another in a longitudinal direction of the instrument, wherein the first and third roller pairs are arranged on a first side of a middle axis of the instrument and the second and fourth roller pairs are arranged on a second side of the middle axis of the instrument, deflecting rollers of the first and fourth roller pairs have a smaller diameter than deflecting rollers of the second and third roller pairs, the joint comprising a double joint and the instrument head bring connected to the shank via the double joint, the instrument head being bendable via at least one roller body pairing of a toothed roller body arranged at the shank side and of a toothed roller body arranged at the instrument head side, wherein a covering part is arranged at the outer side of the first and fourth deflecting roller pairs which is at the outside with respect to the middle axis of the instrument and an actuation disk, which is coupled in movement to the first pair of pull cables, is positively connected to the toothed roller body arranged at the head side via a slot nut.

* * * * *